United States Patent [19]

Aumueller et al.

[11] Patent Number: 5,504,211

[45] Date of Patent: Apr. 2, 1996

[54] POLYALKYLPIPERIDINYL-CONTAINING β-AMINOACRYLIC ESTER DERIVATIVES

[75] Inventors: Alexander Aumueller, Neustadt; Alfred Krause, Schwetzingen; Hubert Trauth, Dudenhofen, all of Germany

[73] Assignee: BASF Aktiengesellschaft, Ludwigshafen, Germany

[21] Appl. No.: 244,202

[22] PCT Filed: Nov. 20, 1992

[86] PCT No.: PCT/EP92/02672

§ 371 Date: May 31, 1994

§ 102(e) Date: May 31, 1994

[87] PCT Pub. No.: WO93/11111

PCT Pub. Date: Jun. 10, 1993

[30] Foreign Application Priority Data

Nov. 30, 1991 [DE] Germany .................. 41 39 606.5

[51] Int. Cl.⁶ .............. C07D 211/00; C07D 401/00; C08K 5/34
[52] U.S. Cl. .............. 546/190; 546/186; 544/360; 544/100; 544/102; 544/103
[58] Field of Search ............. 546/190; 544/360; 546/186; 524/100, 102, 103

[56] References Cited

U.S. PATENT DOCUMENTS 4,468,488  8/1984  Minegawa et al. ............ 524/99
4,769,457  9/1988  Helwig et al. ............ 544/180

*Primary Examiner*—Shean C. Wu
*Attorney, Agent, or Firm*—Oblon, Spivak, McClelland, Maier & Neustadt

[57] ABSTRACT

A polyalky-piperidinyl-containing β-aminoacrylic ester derivative represented by the formula I

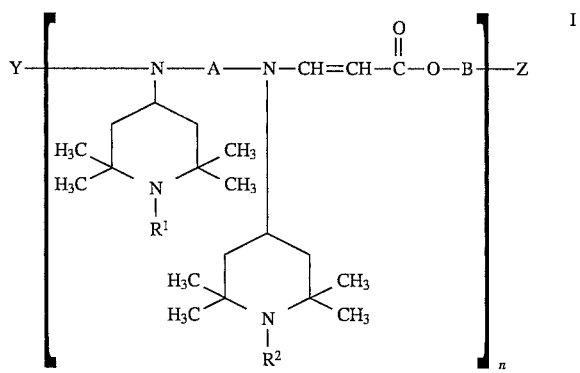

is useful in stabilizing plastic and paints against light, oxygen and heat.

9 Claims, No Drawings

POLYALKYLPIPERIDINYL-CONTAINING β-AMINOACRYLIC ESTER DERIVATIVES

The present invention relates to novel polyalkyl-piperidinyl-containing β-aminoacrylic ester derivatives of the general formula I

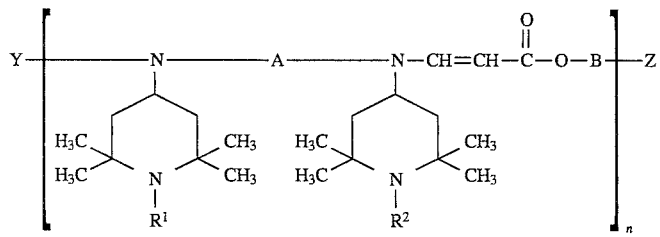

where n is from 1 to 50, $R^1$ and $R^2$ are identical or different and each is hydrogen, $C_1$–$C_6$-alkyl, formyl, $C_2$–$C_6$-alkanoyl, $C_1$–$C_{12}$-alkoxy, $C_5$–$C_6$-cycloalkoxy, cyanomethyl, 2-hydroxyethyl, benzyl or a radical of the formula —$CR^3$=CH—CO—$OR^4$, and $R^3$ is hydrogen, $C_1$–$C_6$-alkyl or a radical of the formula —CO—$OR^4$ and $R^4$ is $C_1$–$C_{18}$-alkyl, $C_5$–$C_8$-cycloalkyl, $C_7$–$C_{18}$-aralkyl, phenyl or tolyl, A is $C_2$–$C_{12}$-alkylene, $C_5$–$C_8$-cycloalkylene, phenylene, biphenylene or a radical of the formula

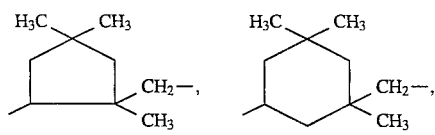

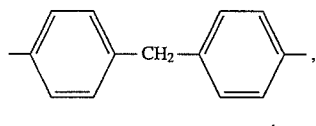

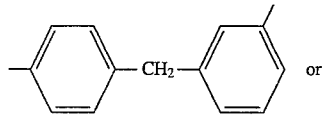 or

-continued

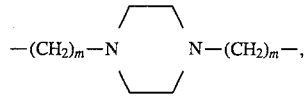

wherein m is 2 or 3, and when n=1

Y is hydrogen, $C_1$–$C_{18}$-alkyl, formyl, $C_2$–$C_{18}$-alkanoyl, $C_7$–$C_{18}$-aralkyl or a group of the formula —CH=CH—CO—O—Z, B is a direct bond, and Z is $C_1$–$C_{18}$-alkyl, $C_5$–$C_8$-cycloalkyl, $C_7$–$C_{18}$-aralkyl, phenyl, tolyl or a radical of the formula —$(CH_2CH_2O)_p$H or —$[CH(CH_3)CH_2O]_p$H, wherein p is from 1 to 30, and when n>1

Y is hydrogen or a group of the formula —CH=CH—CO—O—X—O—CO—C≡CH

B is a bridge member of the formula —CH=CH—CO—O—X—, in which case Z is bonded through the C—C double bond in B, X is $C_2$–$C_{18}$-alkylene, $C_5$–$C_8$-cycloalkylene, phenylene, biphenylene or a group of the formula —$(CH_2CH_2O)_q CH_2CH_2$— or —$[CH(CH_3)CH_2O]_q CH(CH_3)CH_2$—, wherein q is from 1 to 30, and Z is a group of the formula

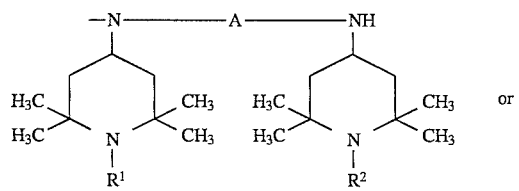

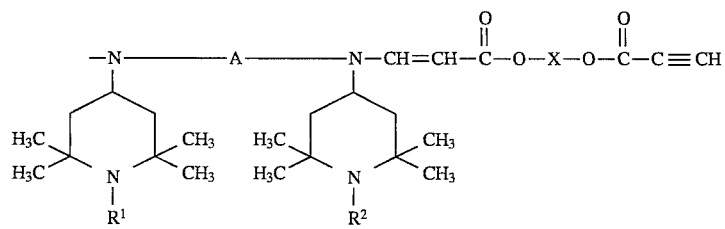

The present invention further relates to organic material, in particular plastics and paints, stabilized against the action of light, oxygen and heat with the compounds I.

Organic material, in particular plastics and paints, is known to be destroyed very rapidly, in particular by the action of light. This destruction customarily takes the form of yellowing, discoloring, cracking or embrittlement of the material. Stabilizers are therefore used to give satisfactory protection from destruction of organic material by light, oxygen and heat.

For instance, EP-A-213 570 describes compounds in which two polyalkylpiperidine groups are linked by a glycoluril bridge via an exocyclic nitrogen atom in the 4-position. These compounds can also exist in polymeric form. They are recommended for use as stabilizers for organic material, in particular for plastics.

What is frequently unsatisfactory with these prior art agents is their low compatibility with plastics, the short duration of their protective effect, their self-color, their volatility and their thermal decomposition when being incorporated at elevated temperatures.

It is an object of the present invention to provide UV absorbers and stabilizers which provide more effective protection of organic material.

We have found that this object is achieved by the polyalkylpiperidinyl-containing β-aminoacrylic ester derivatives I defined at the beginning.

The variable n is preferably from 1 to 10, in particular 1.

$R^1$ and R2 are each preferably hydrogen, methyl or a radical of the formula —CH=CH—CO—OR$^5$, wherein $R^5$ is $C_1$–$C_4$-alkyl. Here $R^1$ and $R^2$ are identical or different.

The variable A is preferably a group of the formula —(CH$_2$)$_k$—, wherein k is from 2 to 12, in particular from 2 to 8.

Very particular preference is give to β-aminoacrylic ester derivatives of the general formula Ia

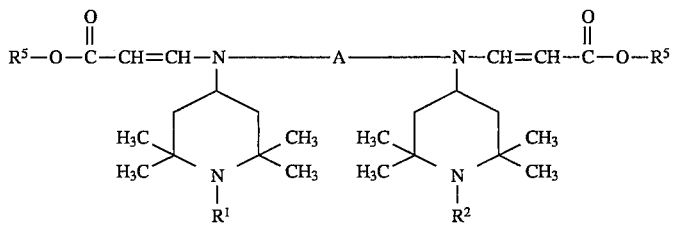

where $R^1$, $R^2$ and A are each as defined above and $R^5$ is $C_1$–$C_4$-alkyl.

Examples of suitable straight-chain or branched alkyl radicals for $R^1$ to $R^5$, Y and Z, described as $C_1$–$C_4$—, $C_1$–$C_6$- and $C_1$–$C_{18}$-alkyl radicals, are methyl, ethyl, n-propyl, isopropyl, n-butyl, isobutyl, sec-butyl, tert-butyl, n-amyl, isoamyl, sec-amyl, tert-amyl, neopentyl, n-hexyl, n-heptyl, n-octyl, 2-ethylhexyl, n-nonyl, isononyl, n-decyl, n-undecyl, n-dodecyl, n-tridecyl, isotridecyl, n-tetradecyl, n-pentadecyl, n-hexadecyl, n-heptadecyl and n-octadecyl. Preference is given in general to lower alkyl radicals, in particular $C_1$–$C_4$-alkyl radicals, especially methyl and ethyl.

As straight-chain or branched alkanoyl for $R^1$ and $R^2$ and for Y, described as $C_2$–$C_6$- and $C_2$–$C_{18}$-alkanoyl, it is possible to use in particular acetyl, but also propionyl, butyryl, isobutyryl, pentanoyl, hexanoyl, heptanoyl, octanoyl, 2-ethylhexanoyl, decanoyl, dodecanoyl, tetradecanoyl, hexadecanoyl and octadecanoyl.

Suitable straight-chain or branched $C_1$–$C_{12}$-alkoxy groups for $R^1$ and $R^2$ are in particular $C_6$–$C_8$-alkoxy groups such as n-hexoxy, isohexoxy, n-heptoxy, isoheptoxy, n-octoxy, 2-ethylhexoxy and isooctoxy but also methoxy, ethoxy, n-propoxy, isopropoxy, n-butoxy, isobutoxy, sec-butoxy, tert-butoxy, n-pentoxy, n-nonoxy, n-decoxy, n-undecoxy and n-dodecoxy.

$C_5$–$C_6$-Cycloalkoxy groups for $R^1$ and $R^2$ are in particular cyclopentoxy and cyclohexoxy.

In a radical of the formula —CR$^3$=CH—CO—OR$^4$ for $R^1$ and $R^2$, $R^3$ is preferably hydrogen or $C_1$–$C_4$-alkoxycarbonyl, especially methoxycarbonyl or ethoxycarbonyl, and $R^4$ is preferably $C_1$–$C_4$-alkyl, especially methyl or ethyl.

Suitable $C_5$–$C_8$-cycloalkyl radicals for $R^4$ and Z are in particular cyclopentyl and cyclohexyl but also cycloheptyl, cyclooctyl, methylcyclopentyl, dimethylcyclopentyl, methylcyclohexyl, ethylcyclohexyl and dimethylcycohexyl.

Suitable $C_7$–$C_{18}$-aralkyl radicals for $R^4$, Y and Z are for example naphthylmethyl, diphenylmethyl or methylbenzyl, but in particular $C_7$–$C_{18}$-phenylalkyl such as 1-phenylethyl, 2-phenylethyl, 1-phenylpropyl, 2-phenylpropyl, 3-phenylpropyl, 2-phenylprop-2-yl, 4-phenylbutyl, 2,2-dimethyl-2-phenylethyl, 5-phenylamyl, 10-phenyldecyl, 12-phenyldodecyl or especially benzyl.

Suitable tolyl is ortho-tolyl, meta-tolyl and in particular p-tolyl.

In a radical Z of the formula —(CH$_2$CH$_2$O )$_p$H or [CH(CH$_3$)CH$_2$O]$_p$H or in a group X of the formula —(CH$_2$CH$_2$O)$_q$CH$_2$CH$_2$— or —[CH(CH$_3$)CH$_2$O]$_q$CH(CH$_3$)CH$_2$—, p and q are each preferably from 1 to 10, in particular from 1 to 5.

The $C_2$–$C_{12}$-alkylene groups for the variable A, which constitutes a bridge member between two polyalkylpiperidine groups for the link via their exocyclic nitrogen atoms in the 4-position, are embodied in particular by polymethylene groups of the formula —(CH$_2$)$_k$—, wherein k is from 2 to 12, in particular from 2 to 8, ie. 1,2-ethylene, 1,3-propylene, 1,4-butylene, pentamethylene, hexamethylene, heptamethylene, octamethylene, nonamethylene, decamethylene, undecamethylene and dodecamethylene. Of these, hexamethylene and 1,2-ethylene are particularly preferred. But it is also possible to employ branched $C_2$–$C_{12}$-alkylene groups, eg. —CH$_2$CH(CH$_3$)CH$_2$—, —CH$_2$C(CH$_3$)$_2$CH$_2$—, —CH$_2$CH(C$_2$H$_5$)— or —CH$_2$CH(CH$_3$)—.

Suitable $C_5$–$C_8$—cycloalkylene groups for A are in particular cyclopentylene, cyclohexylene, cycloheptylene, cyclooctylene, methylcyclopentylene, dimethylcyclopentylene, methylcyclohexylene, dimethylcyclohexylene, ethylcyclohexylene and 1,3- or 1,4-bismethylenecyclohexane.

Phenylene A is ortho- but in particular meta- and para-phenylene. Biphenylene is in particular 3,3'-, 4,4'- and 3,4'-biphenylene.

When n is 1, Y is preferably hydrogen or a group of the formula —CH=CH—CO—O—Z where Z is in particular $C_1$–$C_4$-alkyl. When n>1, Y is preferably hydrogen.

The $C_2$–$C_{18}$-alkylene groups for the bridge member X which is present in the case n>1 are embodied in particular by polymethylene groups of the formula —(CH$_2$)$_l$—, wherein l is from 2 to 18, in particular from 2 to 8, such as 1,2 -ethylene, 1,3-propylene, 1,4-butylene, pentamethylene, hexamethylene, heptamethylene, octamethylene, nonamethylene, decamethylene, undecamethylene, dodecamethylene, tetradecamethylene, hexadecamethylene and octadecamethylene. Of these, hexamethylene and 1,2-ethylene are particularly preferred. But it is also possible to use branched $C_2$–$C_{18}$-alkylene groups, eg. —$CH_2CH(CH_3)CH_2$—, —$CH_2C(CH_3)_2CH_2$—, —$CH_2CH(CH_3)$—, —$CH_2CH(C_2H_5)$— or —$CH_2C(CH_3)_2CH_2CH_2C(CH_3)_2CH_2$—.

Suitable $C_5$–$C_8$-cycloalkylene groups for X are the same as for A.

The remarks concerning phenylene and biphenylene for A also apply to X.

In the case n>1, the end group is preferably a group of the formula

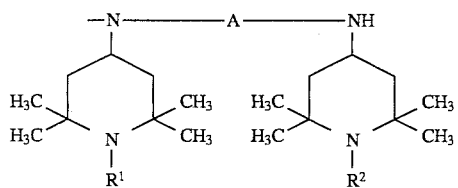

The β-aminoacrylic ester derivatives I according to the invention are advantageously preparable in the case n=1 by reacting polyalkylpiperidine derivatives of the general formula II with propiolic esters of the general formula III

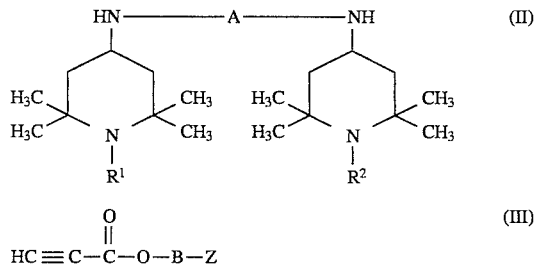

β-Aminoacrylic ester derivatives I in which n>1 are advantageously synthesized by polyaddition of compounds II to bispropiolic esters of the general formula IV.

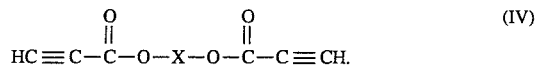

This reaction can be carried out without any solvent or in an inert organic solvent, in water or in mixtures thereof.

Suitable inert organic solvents for this reaction are for example aromatics such as benzene, toluene, xylene, mesitylene, chlorobenzene, nitrobenzene or dichlorobenzene, ethers such as glycol dimethyl ether, glycol diethyl ether or methyl tert-butyl ether, etherols such as glycol monomethyl ether, glycol monoethyl ether or glycol monobutyl ether, amides such as dimethylformamide or dimethylacetamide, esters such as butyl acetate, ethyl acetate, methyl propionate, methyl benzoate or ethyl benzoate, or alcohols such as methanol, ethanol, n-propanol, isopropanol, n-butanol, isobutanol, tert-butanol or glycol.

It is advantageous to employ elevated temperatures, for example within the range from 40° to 150° C., preferably within the range from 80° to 100° C., and atmospheric pressure.

The compounds I according to the invention can be present in the form of the free bases or as salts. Suitable anions are derived for example from inorganic acids and in particular from organic carboxylic acids and also organic sulfonic acids.

Suitable inorganic anions are for example chloride, bromide, sulfate, dicyanimide, methosulfate, tetrafluoroborate, phosphate and thiocyanate.

Suitable carboxylic acid anions are for example formate, acetate, propionate, hexanoate, cyclohexanoate, lactate, stearate, dodecylbenzoate, acrylate, methacrylate, citrate, malonate and succinate and also anions of polycarboxylic acids having up to 3000 COOH groups.

Sulfonic acid anions are for example benzenesulfonate and tosylate.

The compounds of the invention are highly suitable for stabilizing organic material against the action of light, oxygen and heat. They also act as metal deactivators. They are added to the organic material to be stabilized in a concentration of from 0.01 to 5% by weight, preferably from 0.02 to 2% by weight, based on the organic material, before, during or after its preparation.

Organic material for the purposes of the present invention encompasses for example cosmetic products such as creams and lotions, pharmaceutical formulations such as pills and suppositories, photographic recording materials, in particular photographic emulsions, and also intermediates for plastics and paints, but in particular the plastics and paints themselves.

The present invention also provides light-, oxygen- and heat-stabilized organic material, in particular plastics and paints, containing one or more of the compounds I in the above-specified concentrations.

To blend in the compounds I of the present invention, especially into plastics, it is possible to use any known apparatus and method for mixing stabilizing or other additives into polymers.

The organic material stabilized by the compounds I of the present invention may contain other additives, for example antioxidants, light stabilizers, metal deactivators, antistats, flame retardants, pigments and fillers.

Antioxidants and light stabilizers which may be added in addition to the compounds of the present invention are for example compounds based on sterically hindered phenols or sulfur- or phosphorus-containing costabilizers.

Such phenolic antioxidants are for example 2,6-di-tert-butyl-4-methylphenol, n-octadecyl β-(3,5-di-tert-butyl-4-hydroxyphenyl)propionate, 1,1,3-tris(2-methyl 4-hydroxy-5-tert-butylphenyl)butane, 1,3,5-tri-methyl- 2,4,6-tris(3,5-di-tert-butyl-4-hydroxybenzyl)benzene, 1,3,5-tris(3, 5-di-tert-butyl-4-hydroxybenzyl) isocyanurate, 1,3,5-tris[β-(3,5-di-tert-butyl-4-hydroxyphenyl)propionylethyl] isocyanurate, 1,3,5-tris(2,6-dimethyl-3-hydroxy-4-tert-butylbenzyl) isocyanurate and pentaerythritol tetrakis[β-(3, 5-di-tert-butyl-4-hydroxyphenyl)propionate].

As phosphorus-containing antioxidants it is possible to use for example tris(nonylphenyl) phosphite, distearyl pentaerythritol diphosphite, tris(2,4-di-tert-butylphenyl)phosphite, tris(2-tert-butyl-4-methylphenyl) phosphite, bis(2,4-di-tert-butylphenyl) pentaerythritol diphosphite and tetrakis(2,4-di-tert-butylphenyl) 4,4'-bi-phenylene diphosphite.

As sulfur-containing antioxidants it is possible to use for example dilauryl thiodipropionate, dimyristyl thiodipropionate, distearyl thiodipropionate, pentaerythritol tetrakis(β-lauryl thiopropionate) and pentaerythritol tetrakis(β-hexyl thiopropionate).

Further antioxidants and light stabilizers which can be used together with the compounds I of the present invention are for example 2-(2'-hydroxyphenyl)benzotriazoles, 2-hydroxybenzophenones, aryl esters of hydroxybenzoic acids, α-cyanocinnamic acid derivatives, benzimidazolecarboxanilides, nickel compounds and oxalodianilides.

Suitable plastics for stabilization by the compounds I of the present invention are for example:

- polymers of mono- and diolefins, eg. low or high density polyethylene, polypropylene, linear polybutene-1, polyisoprene, polybutadiene and also copolymers of mono- or diolefins or mixtures thereof;
- copolymers of mono- or diolefins with other vinyl monomers, eg. ethylene-alkyl acrylate copolymers, ethylene-alkyl methacrylate copolymers, ethylene-vinyl acetate copolymers or ethylene-acrylic acid copolymers;
- polystyrene;
- copolymers of styrene or α-methylstyrene with dienes and/or acryloyl derivatives, eg. styrene-butadiene, styrene-acrylonitrile (SAN), styrene-ethyl methacrylate, styrene-butadiene-ethyl acrylate, styrene-acrylonitrile-methyl acrylate, acrylonitrile-butadienestyrene (ABS) or methyl methacrylate-butadiene-styrene (MBS);
- halogen-containing polymers, eg. polyvinyl chloride, polyvinyl fluoride, polyvinylidene fluoride and copolymers thereof;
- polymers derived from α,β-unsaturated acids and derivatives thereof, such as polyacrylates, polymethacrylates, polyacrylamides and polyacrylonitriles;
- polymers derived from unsaturated alcohols and amines or from acryloyl derivatives or acetals thereof, eg. polyvinyl alcohol and polyvinyl acetate;
- polyurethanes, polyamides, polyureas, polyesters, polycarbonates, polysulfones, polyether sulfones and polyether ketones.

The compounds I of the present invention can also be used for stabilizing coatings, eg. industrial coatings. They are especially suitable for baking finishes, in particular automotive coatings, preferably two-layer coatings.

The compounds I of the present invention can be added to the coating composition in a solid or dissolved form. Their ready solubility in coating systems is of particular advantage here.

Preferably, the compounds I of the present invention are used for stabilizing polyamides and ABS and SAN polymers, in particular molding materials prepared therefrom, and also surface coatings.

A further preferred field of use is the stabilization of polypropylene and polyamide, in particular fibres thereof.

The compounds I of the present invention are highly compatible with customary types of plastic and readily soluble in conventional coating systems. In general, they have only minimal self-color, if any, are stable and nonvolatile at the customary plastic and paint processing temperatures, and in particular confer a long period of protection on the materials treated therewith.

The invention is further illustrated by the examples which follow. The synthesis conditions have not been optimized.

PREPARATION EXAMPLES

EXAMPLE 1

78.8 g of N,N'-bis(2,2,6,6-tetramethyl-4-piperidinyl)hexamethylenediamine were introduced in 300 ml of ethanol. 40 g of ethyl propiolate were added dropwise with stirring at room temperature, and the temperature then rose to 50° C. This was followed by heating at the boil for 1 h, cooling down to 5° C. and the dropwise addition of 600 ml of water, which brought down white crystals. Filtration and drying left 112 g of the compound of the formula

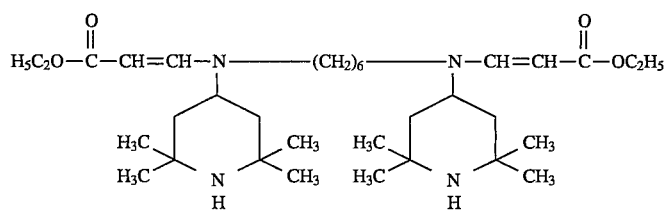

as a colorless solid of melting point 122°–129° C. The compound was further purified by recrystallization from acetonitrile, and the melting point rose to 126°–130° C.

Analysis: Calculated C 69.1 H 10.6 N 9.5 Found C 68.8 H 10.6 N 9.4

EXAMPLE 2a 96 g of propiolic acid, 66.6 g of 1,6-hexanediol and 0.2 ml of concentrated sulfuric acid were heated in 600 ml of n-hexane under a water separator for 13 h, until the removal of water ceased. Two phases were obtained on cooling. The bottom phase was discharged into 1 l of water and stirred therein at room temperature for 1 h, which resulted in the formation of a colorless solid precipitate. Filtration and drying left 115 g of the bispropiolic ester of the formula

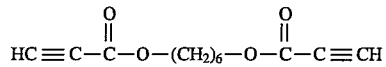

of melting point 45°–47° C.

EXAMPLE 2b

To a solution of 19.7 g of N,N'-bis(2,2,6,6-tetramethyl-4-piperidinyl)hexamethylenediamine in 50 ml of dimethylformamide was added dropwise at 50° C. a solution of 11.1 g of the bispropiolic ester of the Example 2a in 30 ml of dimethylformamide. In the course of the addition the internal temperature rose to 76° C. After 4 h at 70° C. the reaction solution was cooled back down to room temperature and 1.5 l of water were added dropwise with vigorous stirring. The resulting precipitate was filtered off and dried under reduced pressure. This left 23.4 g of the oligomer of the formula

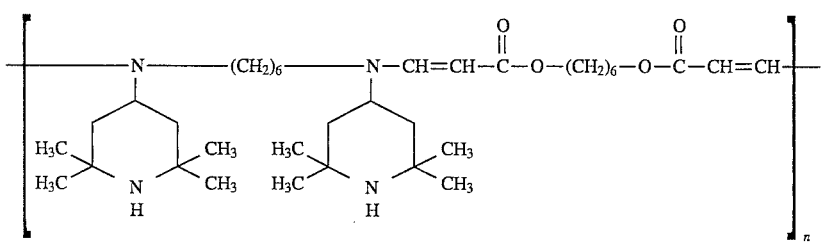

of melting point 105° C. The average value for n was 7.1.

Analysis: Calculated C 70.1 H 10.5 N 9.1 Found C 68.8 H 10.5 N 9.2

EXAMPLE 3

To a solution of 78.8 g of N,N'-bis-(2,2,6,6-tetramethyl-4-piperidinyl)hexamethylenediamine in 300 ml of ethanol were added dropwise without cooling 80 g of ethyl propiolate over 1 h, in the course of which the temperature rose from 20° C. to 58° C. After refluxing for 2 h the reaction mixture was cooled down to 5° C., and the precipitate was filtered off, washed with 100 ml of cold ethanol and dried at 100° C. in a water jet vacuum. This gave 132.5 g of the compound of the formula

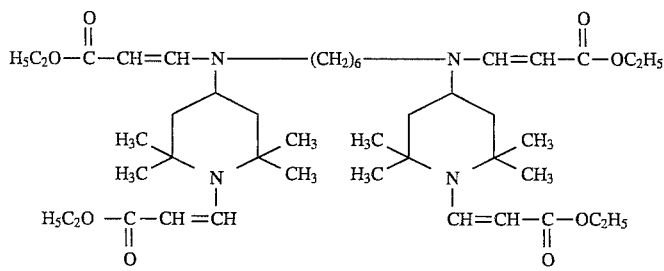

as a colorless solid of melting point 184°–187° C.

Analysis: Calculated C 67.1 H 9.5 N 7.1 Found C 67.0 H 9.6 N 7.2

We claim:

1. Polyalkylpiperidinyl-containing β-aminoacrylic ester derivatives of the general formula I

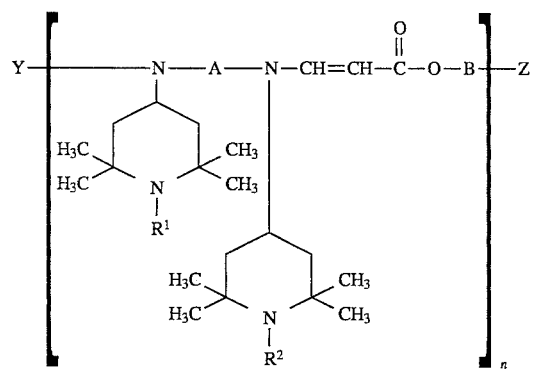

where n is from 1 to 50, $R^1$ and $R^2$ are identical or different and each is hydrogen, $C_1$–$C_6$-alkyl, formyl, $C_2$–$C_6$-alkanoyl, $C_1$–$C_{12}$-alkoxy, $C_5$–$C_6$-cycloalkoxy, cyanomethyl, 2-hydroxyethyl, benzyl or a radical of the formula —$CR^3$=CH—CO—$OR^4$, and $R^3$ is hydrogen, $C_1$–$C_6$-alkyl or a radical of the formula —CO—$OR^4$ and $R^4$ is $C_1$–$C_{18}$-alkyl, $C_5$–$C_8$-cycloalkyl, $C_7$–$C_{18}$-aralkyl, phenyl or tolyl, A is $C_2$–$C_{12}$-alkylene, $C_5$–$C_8$-cycloalkylene, phenylene, biphenylene or a radical of the formula

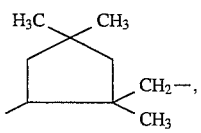 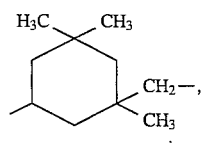

-continued

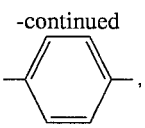

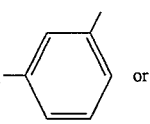

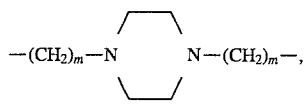

wherein m is 2 or 3, and when n=1

Y is hydrogen, $C_1$–$C_{18}$-alkyl, formyl, $C_2$–$C_{18}$-alkanoyl, $C_7$–$C_{18}$-aralkyl or a group of the formula —CH=CH—CO—O—Z, B is a direct bond, and Z is $C_1$–$C_{18}$-alkyl, $C_5$–$C_8$-cycloalkyl, $C_7$–$C_{18}$-aralkyl, phenyl, tolyl or a radical of the formula —$(CH_2CH_2O)_p$H or —$[CH(CH_3)CH_2O]_p$H, wherein p is from 1 to 30, and when n>1

Y is hydrogen or a group of the formula —CH=CH—CO—O—X—O—CO—C=CH

B is a bridge member of the formula —CH=CH—CO—O—X—, in which case Z is bonded through the C—C double bond in B, X is $C_2$–$C_{18}$-alkylene, $C_5$–$C_8$-cycloalkylene, phenylene, biphenylene or a group of the formula —$(CH_2CH_2O)_qCH_2CH_2$— or —$[CH(CH_3)CH_2]_qCH(CH_3)CH_2$—, wherein q is from 1 to 30, and Z is a group of the formula

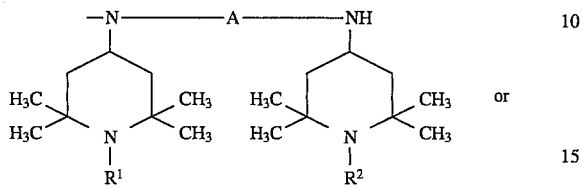

or

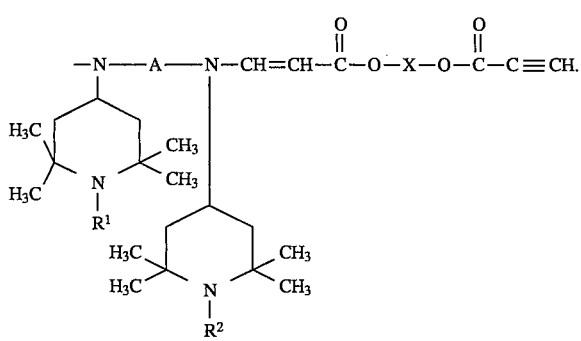

2. β-Aminoacrylic ester derivatives I as claimed in claim 1, wherein n is from 1 to 10.

3. β-Aminoacrylic ester derivatives I as claimed in 1, wherein $R^1$ and $R^2$ are identical or different and each is hydrogen, methyl or a radical of the formula —CH=CH—CO—$OR^5$, wherein $R^5$ is $C_1$–$C_4$-alkyl.

4. β-Aminoacrylic ester derivatives I as claimed in claim 1 wherein A is a group of the formula —$(CH_2)_k$—, wherein k is from 2 to 12.

5. β-Aminoacrylic ester derivatives of the general formula Ia as claimed in claim 1.

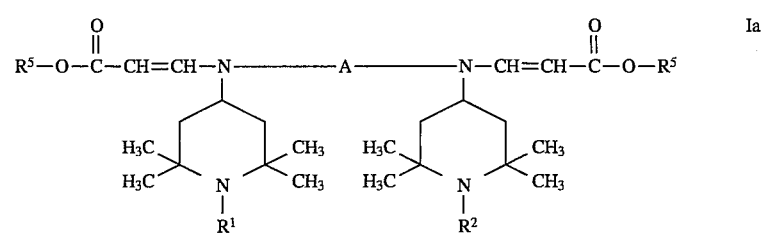

where $R^1$, $R^2$ and A are each as defined above and $R^5$ is $C_1$–$C_4$-alkyl.

6. A light-, oxygen- and heat-stabilized organic material containing from 0.01 to 5% by weight, based on the amount of the organic material, of one or more β-aminoacrylic ester derivatives I as claimed in claim 1.

7. A light-, oxygen- and heat-stabilized plastic or paint containing from 0.01 to 5% by weight, based on the amount of the plastic or paint, of one or more β-aminoacrylic ester derivatives I as claimed in claim 1.

8. A process for stabilizing organic material against the action of light, oxygen and heat, which comprises using for this purpose β-aminoacrylic ester derivatives I as claimed in claim 1.

9. A process for stabilizing plastics and paints against the action of light, oxygen and heat, which comprises using for this purpose β-aminoacrylic ester derivatives I as claimed in claim 1.

* * * * *